United States Patent [19]

Kubota

[11] Patent Number: 5,192,754

[45] Date of Patent: Mar. 9, 1993

[54] FISH STRESS RESISTANCE METHOD

[75] Inventor: Saburo Kubota, Akishima, Japan

[73] Assignee: Roussel Uclaf, Paris, France

[21] Appl. No.: 833,768

[22] Filed: Feb. 11, 1992

[30] Foreign Application Priority Data

Feb. 13, 1991 [JP] Japan .................................. 3-40648

[51] Int. Cl.$^5$ .............................................. A61K 31/56
[52] U.S. Cl. ..................................... 514/170; 514/171
[58] Field of Search ............................... 514/170, 171

[56] References Cited

FOREIGN PATENT DOCUMENTS 2428440 2/1980 France .

OTHER PUBLICATIONS

Chemical Abstracts (95:112060m) 1981.

Primary Examiner—Frederick E. Waddell
Assistant Examiner—K. Weddington

Attorney, Agent, or Firm—Bierman and Muserlian

[57] ABSTRACT

A method of relieving stress in fish and increasing resistance to pathogenic agents comprising orally administering to the fish an amount of a compound of the formula

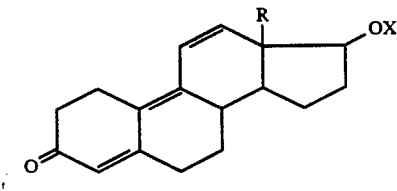

wherein R is alkyl of 1 to 4 carbon atoms and X is acyl of an organic carboxylic acid of 1 to 18 carbon atoms sufficient to relieve stress and increase resistance to pathogenic agents and novel fish feed containing an effective amount of a compound of formula I.

6 Claims, 6 Drawing Sheets

FISH STRESS RESISTANCE METHOD

STATE OF THE ART

Fish are difficult to rear and their health is directly linked to the medium in which they evolve. Therefore, any variation of the medium can be a stress factor for fish. Among the stress factors, there can be mentioned: a) physical factors such as variations of water temperature and variations of gas dissolved in the water, b) mechanical factors due to transport and overcrowding of fish in a given place and c) chemical or biological factors due to bacteria, viruses and parasites.

Fish are very stress sensitive and every time one transfers them from tank to tank, tank to pond or during the grading using nets, one creates important stress reactions. The stress reaction induce important modifications; namely 1) Internal: Discharge of catecholamines and corticosteroids which greatly modify blood parameters, metabolism and excretion and 2) External: The epidermis of fish is much less thick than upper vertebrate and does not contain keratin. The epidermis covers the scales and is very easily damaged and scratched during manipulation.

Very often after handling, disease outbreaks and mortality occurs with variable intensity depending on the species and the age of the fish and the know-how of the farmer. Reducing this manipulation mortality could be a break-through in aquaculture.

A more particular subject of the invention is the use of trenbolone acetate (TBA) for the manufacture of anti-stress medicated feed intended for administration to fish.

OBJECTS OF THE INVENTION

It is an object of the invention to provide a novel method of relieving stress and increasing resistance to pathogenic agents in fish.

It is another object of the invention to provide improved fish feed.

These and other objects and advantages of the invention will obvious from the following detailed description.

THE INVENTION

The novel method of the invention of relieving stress in fish and increasing resistance to pathogenic agents comprises orally administering to the fish an amount of a compound of the formula

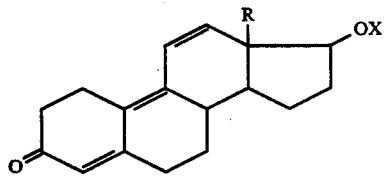

wherein R is alkyl of 1 to 4 carbon atoms and X is acyl of an organic carboxylic acid of 1 to 18 carbon atoms sufficient to relieve stress and increase resistance to pathogenic agents. R is preferably methyl and X is preferably acetoxy, amyloxy or hexahydrobenzoxycarbonyl.

Excellent results have been obtained with fresh water fish, salt water fish and brackish fish. For example, excellent results have been obtained in Salmonidae such as trout or salmon, in Anguillidae such as eels, in Cyprinidae such as carp, in cyclid fish such as tilapia and in sea fish such as sea bass or sea bream.

From the experimental work discussed infra, the following favorable histological results have been shown; 1) Less fatty degeneration of the pancreas in the treated group than in controls and better irrigation of the organ; improved insulin secretion from Langerhans islets and; improved digestive enzyme production which ameliorates the food utilization 2) Less fatty deposition in the liver in the treated group, improved irrigation and thus amelioration of liver functions; namely Depuration and Synthesis, and 3) thickening of the epidermis and decrease in the fatty infiltration of the subcutaneous muscle.

In a preferred method of the invention, the compounds of formula I are administered orally by incorporating the same in the fish feed. As fish feed, commercially sold mixtures containing fish meals, proteins, yeasts, soya meal and vitamins which are often presented in the form of powders or granules can be used. A more particular subject of the invention is the method of treating salmon, trout or eel. The compounds of formula I are incorporated in a fish feed at the rate of 1 to 20 ppm of active ingredient per weight of fish feed, for example at the rate of 5 to 15 ppm.

The method of the invention is particularly useful to increase the resistance of fish to stress in fish farming and to increase resistance of fish to fungi, viruses, bacteria and other pathogenic agents, particularly when the pathogenic agent is Saprolegnia which is quite remarkable because it is a pathogenic agent which is difficult to treat.

Very good results have been obtained using the method of the invention as a treatment 20 to 30 days before the factor which will induce stress, for example before tank transfer. The daily dosage can be from 0.1 to 0.5 mg per kg of fish body weight per day.

In the following examples, there are described several preferred embodiments to illustrate the invention. However, it is to be understood that the invention is not intended to be limited to the specific embodiments.

EXAMPLE 1

A powder for administration to fish was prepared by incorporating 10 mg of 17 $\beta$-acetoxy-$\Delta^{4,9,11}$-estratriene-3-one per 1000 g of powder.

EXAMPLE 2

A fish feed was prepared by homogenously admixing 1000 g of flour, 700 g of water, 70 g of arachid oil and 17.7 mg of 17 $\beta$-acetoxy-$\Delta^{4,9,11}$-estratriene-3-one which is equivalent to 10 mg of steroid per kg of feed.

BIOLOGICAL STORY

1) Test method

Fish, Oncorhynchus kisutch (Coho Salmon) raised in an aquaculture pond were released into rearing tanks on day 0 with each group consisting of 70 fish. All the fish were apparently normal and similar in body size (with extremely large or small ones excluded), with an average body weight of 22.2 to 22.4 g in each tank. The fish were baited while being acclimated and were fed so that they would take feed which in total, corresponded to 1.8% (in weight) of the total body weight of the fish in each tank. On day 6, feed intake by the fish was completely stabilized, and on that day, TBA, 17 $\beta$-acetoxy-$\Delta^{4,9,11}$-estratriene-3-one administration was started. The administrtion was terminated on day 25. During those 25 days, feed was given on 21 days (excluding Sundays) in an amount corresponding to 1.8% of the body weight of fish, both in the treated groups and the control groups.

Feed was prepared in the following way: To the feed for trout (powder), water which corresponds to half of the feed powder (in volume) and a specified amount of salad oil were added. The mixture was put in a polyethylene bag, and then crumpled up so that it become homogeneous. Next, the mixture was put through a garlic squeezer for the purpose of forming and then dried by air. When preparing feed for the TBA-treated group, TBA was first dissolved in salad oil at a specified rate so that the content of TBA was finally "10 mg/1000 g of feed (10 ppm)" which corresponded to 0.2 to 0.5 mg of TBA per 1000 g body weight".

Rearing conditions

Fish were released into tanks of 30 cm×70 cm×29 cm (water depth: 25 cm) each, with 70 fish per tank. The water temperature was kept at 8.8°-10.2° C. and water flow rate was held at 3-5 liters/minute.

Saprolegniasis test method

In accordance with Dr. Hoshiai's "AMIMOMI" Method (mechanical stress or net shaking stress test), stress was forced on the fish and epithelial damages were made on them. To enhance the reliability of the study, "AMIMOMI" was conducted under varied conditions: the number of fish per "AMIOMI" was 5 or 10, and "AMIMOMI" time was 30 seconds, 1 minute, or 2 minutes.

For the fish to undergo the attack of Saprolegnia zoospores, the fish were released into water containing 2×10 zoospores/liter of water. During the test period, water in the 60×30×45 cm (water depth: 40 cm) tanks was wholly changed every 3 days. Zoospore attack and fish observation lasted for 14 days, from Sep. 22nd to Oct. 6th. During the period, water supply was stopped; aeration was continued; and the water temperature was kept at 12°-13° C. During the rearing period, water was supplied through 2 pipes to take into account the risk of the possible damage of a pipe by accidents, such as heavy rainfall, etc.

2) Results and Discussion Concerning the Infection Test

Test results are shown in FIGS. 1 to 6 as follows: Each figure displays the number of infected fish in the control group and the TBA treated group, and the number of dead fish (only among the control fish, no mortality having been recorded in the TBA treated group).

Day 0 is the day of the stress test.
FIG. 1: stress test: 30 s each on 5 fish.
FIG. 2: stress test: 30 s each on 10 fish.
FIG. 3: stress test: 60 s each on 5 fish.
FIG. 4: stress test: 60 s each on 10 fish.
FIG. 5: stress test: 120 s each on 5 fish.
FIG. 6: stress test: 120 s each on 10 fish.

a) Trend observed in the control groups

Given the same number of fish per "AMIMOMI", the longer the "AMIMOMI" time, the higher the rate of infection was, the earlier the symptoms developed, the higher the mortality was, and the quicker they died. It is because the longer "AMIMOMI" time was, the higher the stress and the more serious the traumas were. Given the same "AMIMOMI" time, the smaller the number of fish per "AMIMOMI" was, the quicker the symptoms developed and the higher the incidence of infection was. The same trend was observed regarding the following parameters, environmental conditions such as the size of tanks, the number of zoospores per tank, rearing water temperature, etc., the smaller the number of fish per "AMIMOMI", the higher the number of attacking zoospores per fish, b) Trend observed in the TBA-treated groups: The trend was generally similar to that observed in the control groups. In the following point, however, the TBA-treated groups showed large differences from the control groups. Among the fish which underwent "AMIMOMI" as a group of 5, infection was confirmed first on the 3rd day and it disappeared on the 6th, regardless of the duration of "AMIMOMI". The longer the "AMIMOMI" was, however, the higher the rate of infection was. In the case of the fish which underwent "AMIMOMI" as a group of 10 and where "AMIMOMI" lasted for 30 seconds, infection was confirmed on the 4th day and disappeared on the 9th day. In the fish which underwent "1-minute "AMIMOMI" as a group of 10, infection was confirmed 1 day earlier, i.e. on the 3rd day, but recovered to normal on the 9th day. In the latter group, rate of infection was higher than that of the "30-second AMIMOMI group The "2-minute AMIMOMI" group showed a trend which was almost the same a that shown in the "1-minute AMIMOMI" group, with all the fish recovering from Saprolegniasis except one in which the disease was still confirmed on the final day. Morever, rate of infection was lower than in the "1-minute AMIMOMI" group.

According to the analysis where conditions of infection were compared among the fish of the same AMIMOMI time group: In the "2-minute AMIMOMI group", rate of infection was much higher than others in the "5-fish AMIMOMI" group. In the 30-second and 1-minute AMIMOMI groups, there was no diference except that 100% recovery was achieved later than in the 2-minute group. Based on the above, it was concluded that when attacked by zoospores, the TBA-treated fish were once infected but soon got rid of the hypha and then recovered. Thus, by being treated with TBA, propyalxis against Saprolegniasis was achieved.

c) Differeences between groups, both in the 5-fish AMIMOMI group and the 10-fish AMIMOMI group, infection was observed 1-2 days later and the degree of infection was remarkably smaller compared with the control groups regrdless of the AMIMOMI duration. If the two groups were compared under the same conditions, in the TBA-treated group, rate of infection was lower, recovery appeared earlier, and there was no death. In the TBA group (10 fish) 2-minute AMIMOMI, only 1 fish did not recover at the completion of the study.

The brief explanation of the drawings.
FIG. 1 is a graph of the results of antifungal activity of TBA when forcing stress on the groups of 5 fish for 30 seconds.

Figure 1:
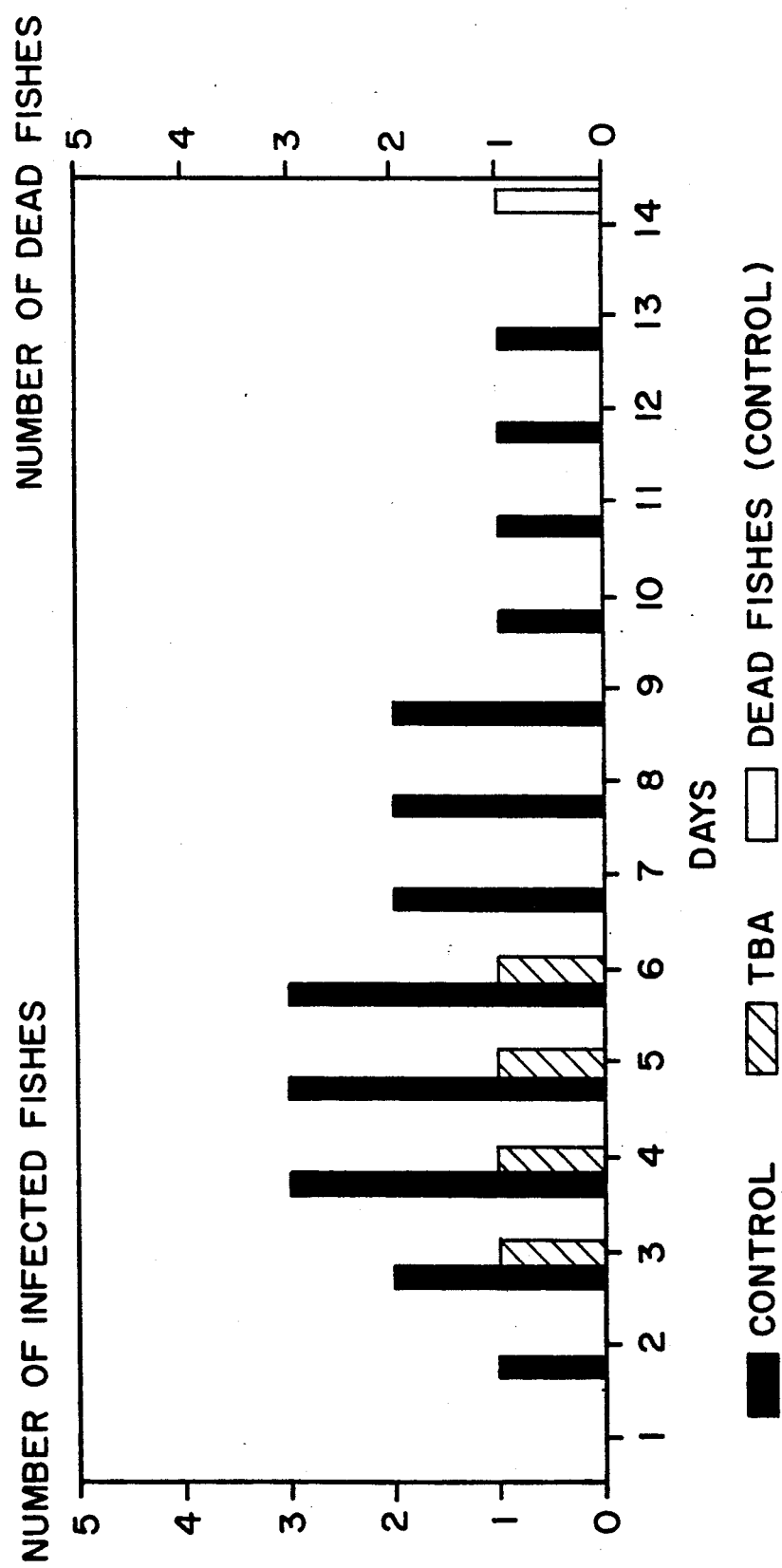
Figure 2:
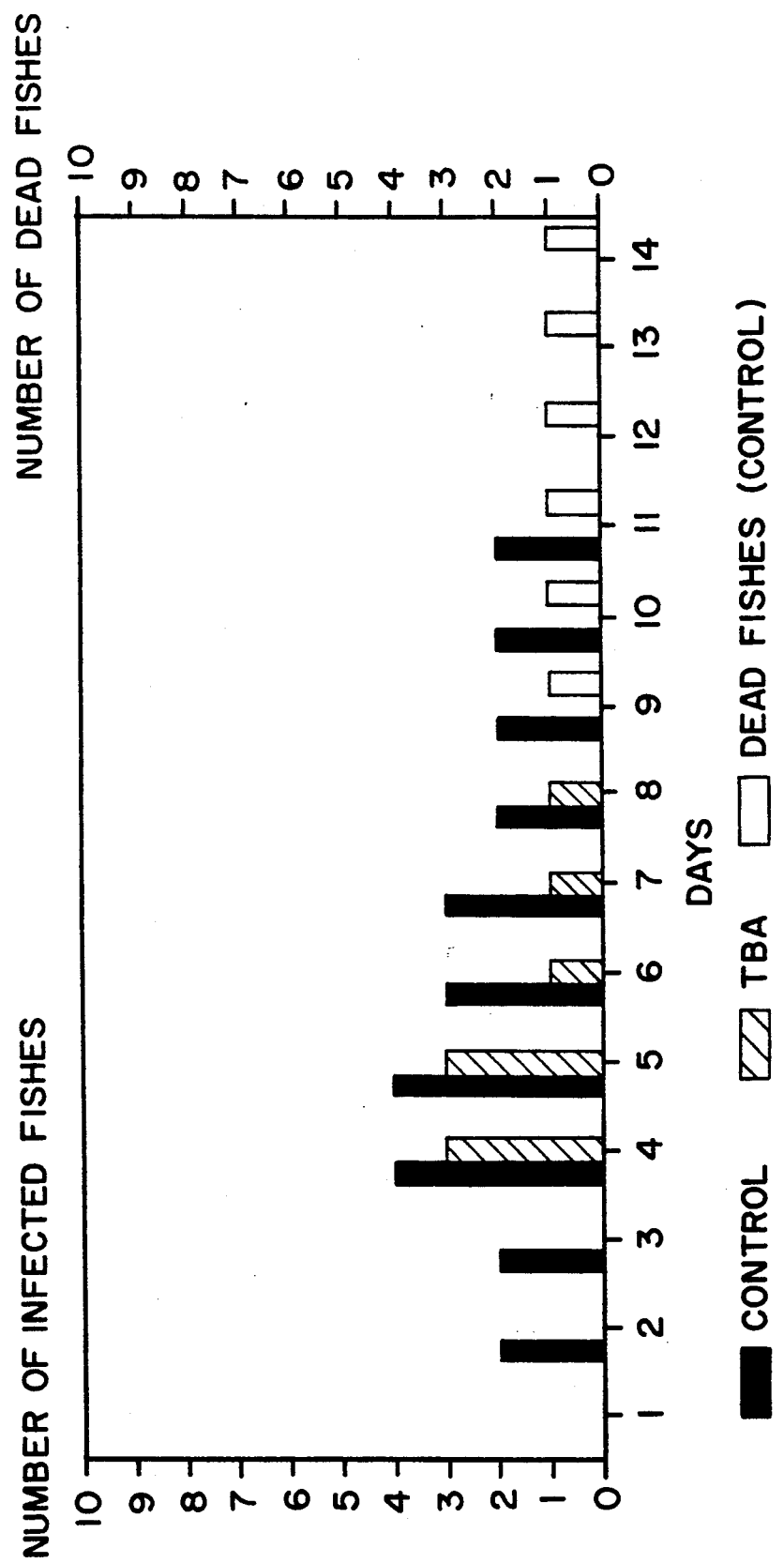
FIG. 2 is a graph of the results of antifungal activity of TBA when forcing stress on the groups of 10 fish for 30 seconds.
Figure 3:
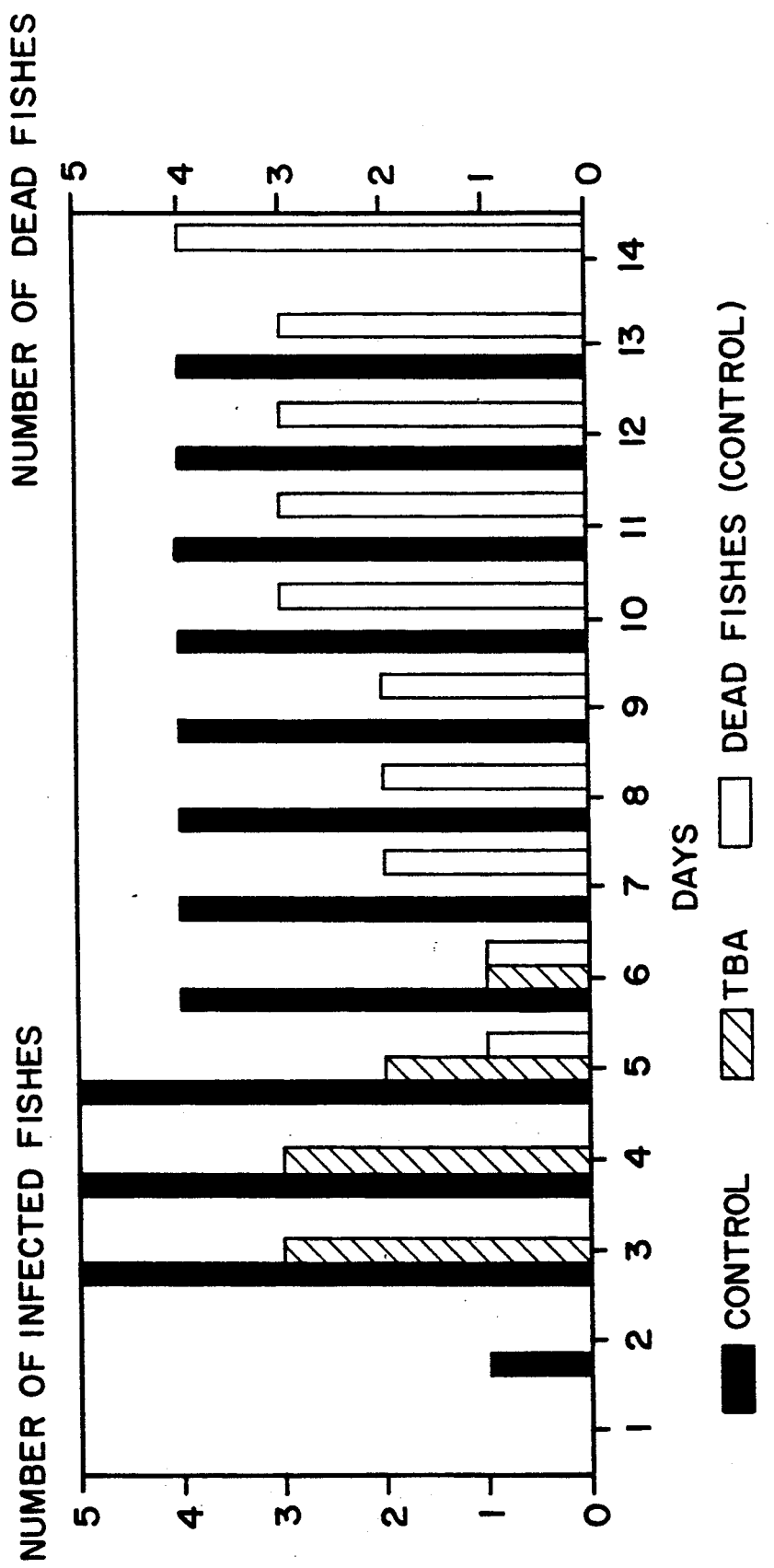
FIG. 3 is a graph of the results of antifungal activity of TBA when forcing stress on the groups of 5 fish for 1 minute.
Figure 4:
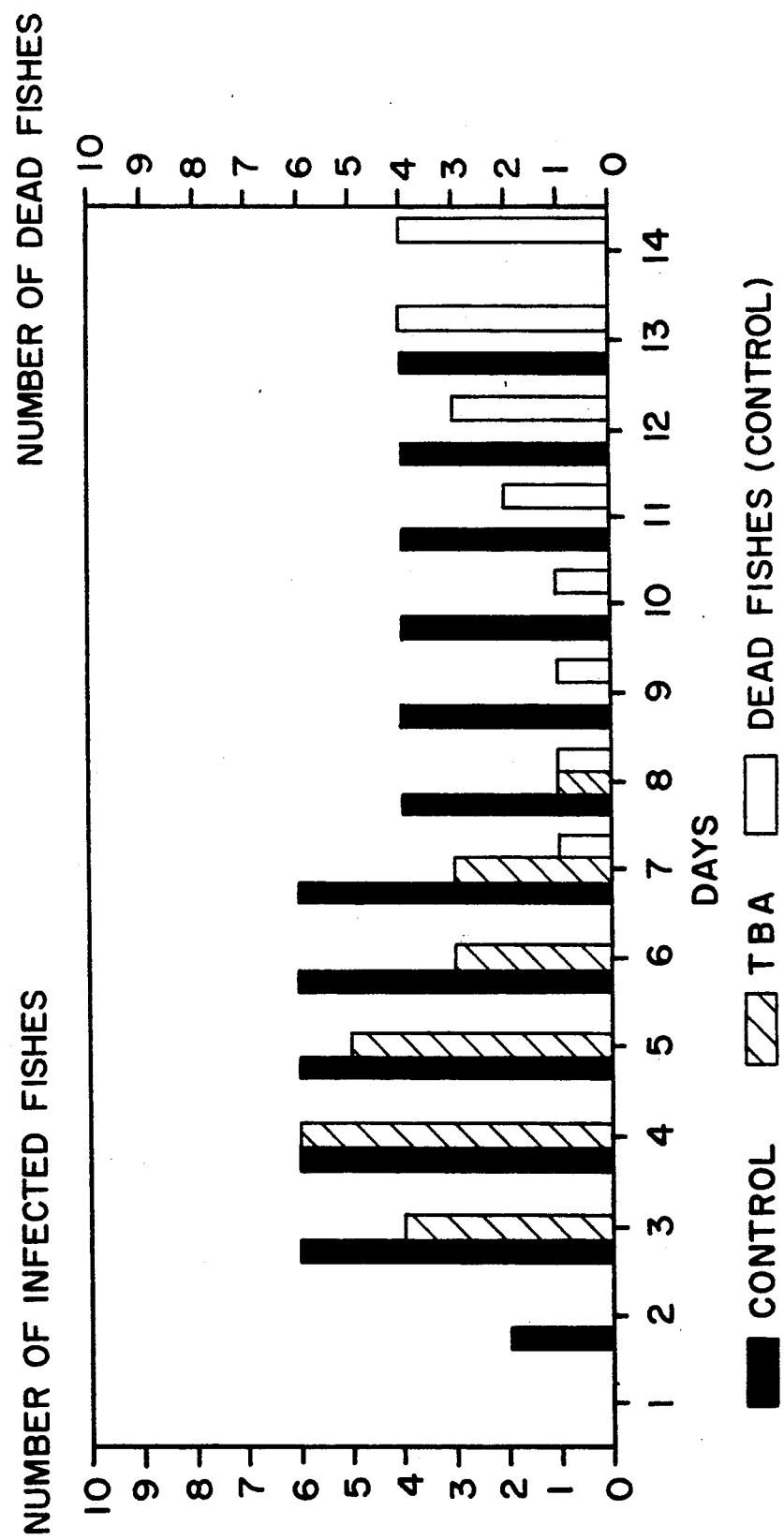
FIG. 4 is a graph of the results of antifungal activity of TBA when forcing stress on the groups of 10 fish for 1 minute.
Figure 5:
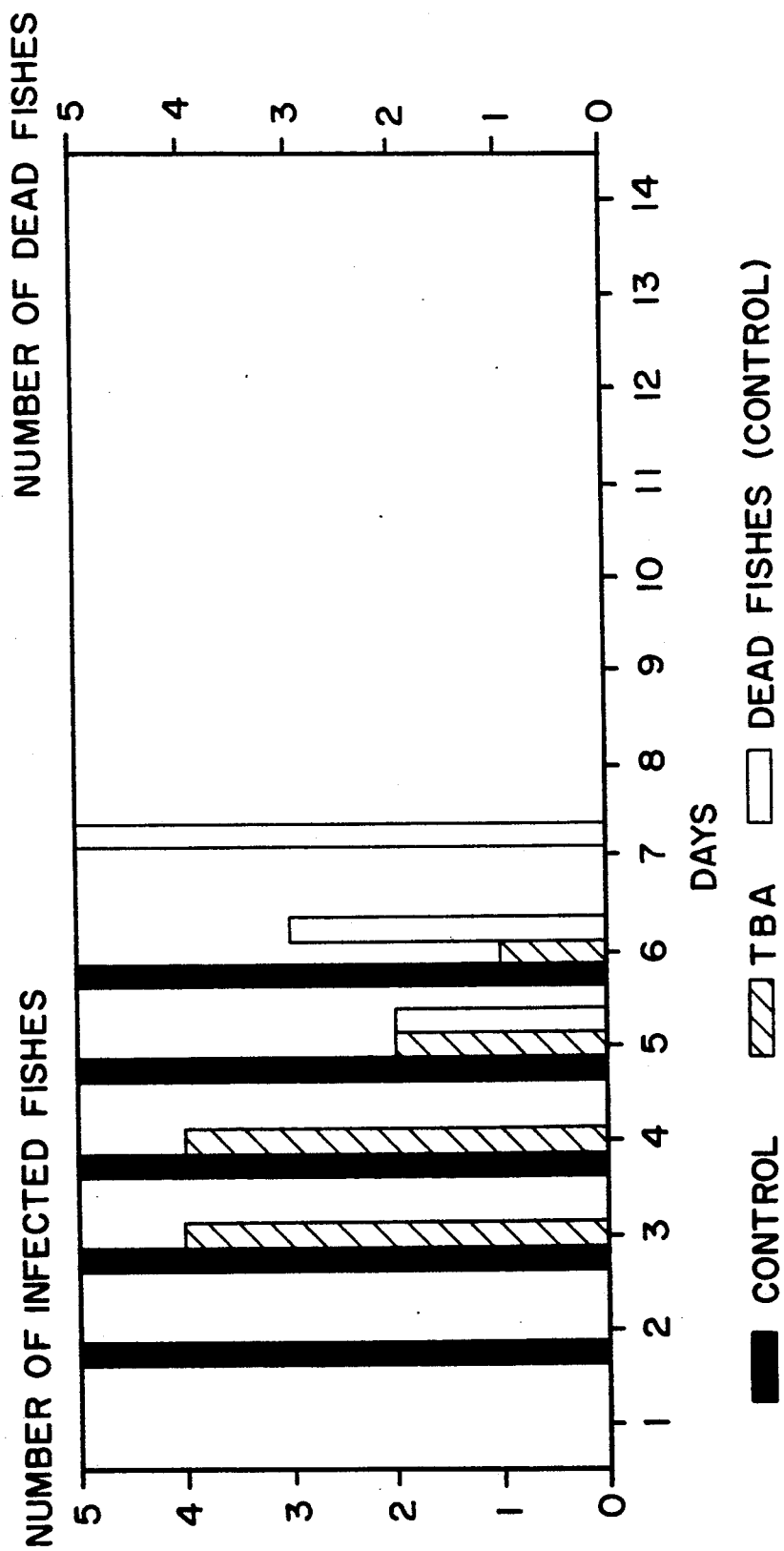
FIG. 5 is a graph of the results of antifungal activity of TBA when forcing stress on the groups of 5 fish for 2 minutes.
Figure 6:
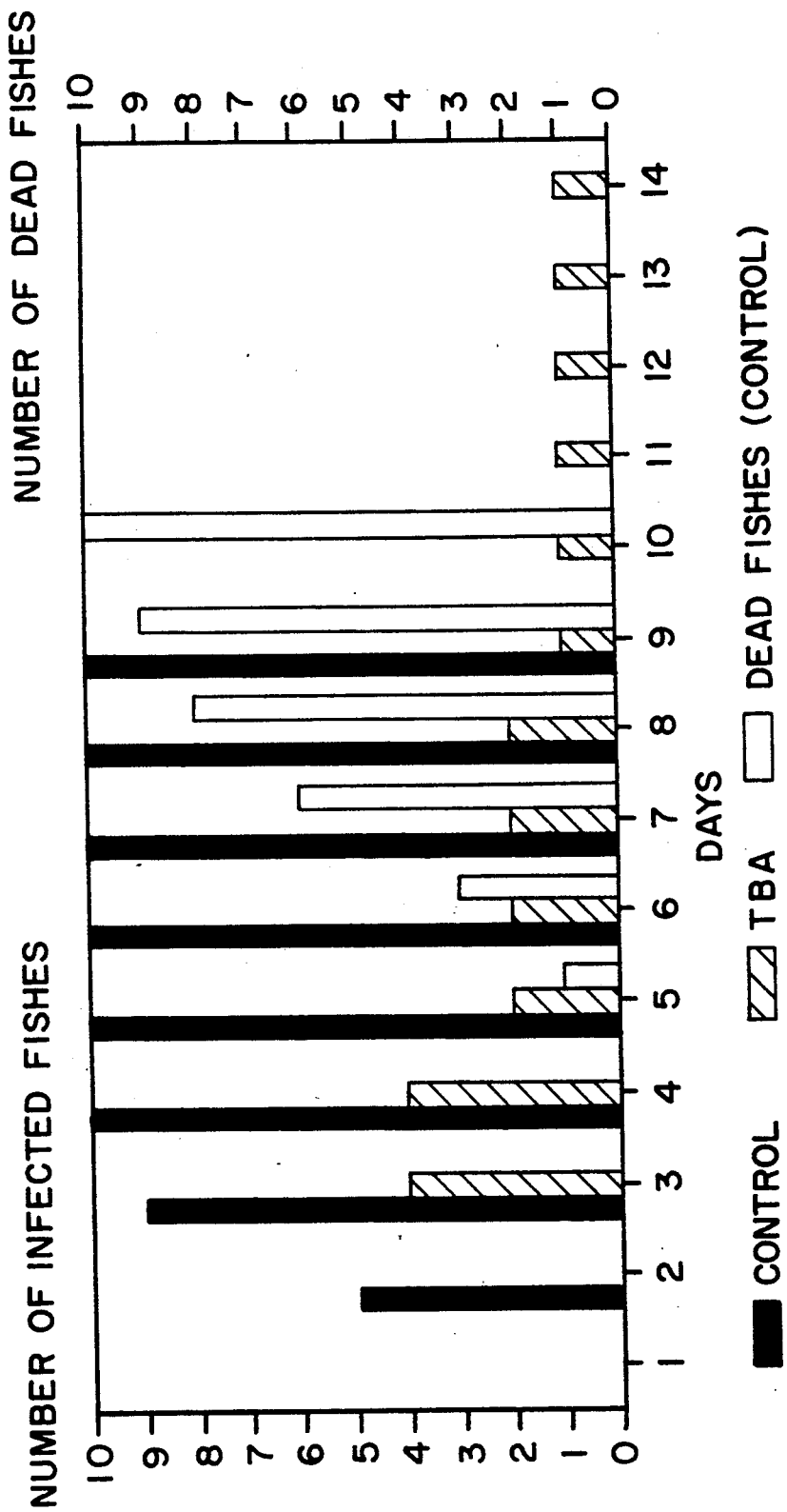
FIG. 6 is a graph of the results of antifungal activity of TBA when forcing stress on the groups of 10 fish for 2 minutes.

Various modifications of the method or feed of the invention may be made without departing from the spirit or scope thereof and it is to be understood that the invention is intended to be limited only as defined in the appended claims.

What I claim is:

1. A method of relieving stress in fish and increasing resistance to pathogenic agents selected from the group consisting of fungi, viruses and bacteria comprising orally administering daily to the fish an amount of 0.1 to 0.5 mg of a compound of the formula

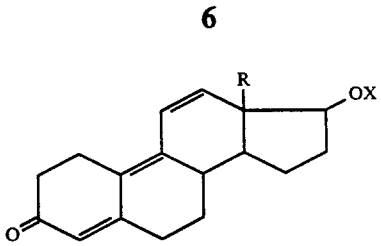

wherein R is alkyl of 1 to 4 carbon atoms and X is acyl of an organic carboxylic acid of 1 to 18 carbon atoms per kg of fish body weight sufficient to relieve stress and increase resistance to fungi, viruses and bacteria.

2. The method of claim 1 wherein R is methyl.

3. The method of claim 2 wherein X is selected from the group consisting of acetoxy, amyloxy and hexahydrobenzoxycarbonyl.

4. The method of claim 1 wherein the compound of formula I is administered with a fish food.

5. The method of claim 1 wherein the fish are selected from the group consisting of Salmonidae, Anguillidae, Cyprinidae, cycloid fish and sea fish.

6. The method of claim 1 wherein the pathogenic agent is Saprolegnia.

* * * * *